US009074266B2

(12) United States Patent
Bisson et al.

(10) Patent No.: US 9,074,266 B2
(45) Date of Patent: Jul. 7, 2015

(54) 2,9-DIPYRIDYL-1,10-PHENANTHROLINE DERIVATIVES USEFUL AS ACTINIDE LIGANDS, METHOD FOR SYNTHESIZING SAME, AND USES THEREOF

(75) Inventors: Julia Bisson, Cherbourg (FR); Marie-Christine Charbonnel, Saint Gervais (FR); Nathalie Boubals, Camaret d'Aigues (FR); Manuel Miguirditchian, Avignon (FR); Denis Guillaneux, Clamart (FR); Dominique Guillaumont, Avignon (FR); Cecile Marie, Avignon (FR); Didier Dubreuil, Port Saint Pere (FR); Muriel Pipelier, Nantes (FR); Virginie Blot, Orvault (FR)

(73) Assignees: Commissariat à l'énergie atomique et aux énergies alternatives, Paris (FR); UNIVERSITE DE NANTES, Nantes (FR)

( * ) Notice: Subject to any disclaimer, the term of this patent is extended or adjusted under 35 U.S.C. 154(b) by 0 days.

(21) Appl. No.: 14/009,292

(22) PCT Filed: Mar. 28, 2012

(86) PCT No.: PCT/EP2012/055557
§ 371 (c)(1), (2), (4) Date: Oct. 15, 2013

(87) PCT Pub. No.: WO2012/130902
PCT Pub. Date: Oct. 4, 2012

(65) Prior Publication Data

US 2014/0030172 A1 Jan. 30, 2014

(30) Foreign Application Priority Data

Apr. 1, 2011 (FR) ..................................... 11 52835

(51) Int. Cl.
*C07D 471/04* (2006.01)
*C22B 60/02* (2006.01)
(Continued)

(52) U.S. Cl.
CPC .......... *C22B 60/0295* (2013.01); *C07D 471/04* (2013.01); *C22B 3/0035* (2013.01);
(Continued)

(58) Field of Classification Search
CPC ............................ C07D 471/04; C22B 3/0035
USPC ............................................................ 546/88
See application file for complete search history.

(56) References Cited

U.S. PATENT DOCUMENTS 8,557,120 B2 10/2013 Heres et al.
2009/0184051 A1 7/2009 Heres et al.
(Continued)

FOREIGN PATENT DOCUMENTS

WO 2007 022307 2/2007
WO WO 2007/118904 A1 10/2007
WO WO 2008/049807 A1 5/2008
WO 2011 009814 1/2011
WO WO 2011/009814 A1 1/2011
WO 2011 030566 3/2011

OTHER PUBLICATIONS

Self-assembling, Chromogenic Receptor for recognition of dicarboxylic acids, Scott Goodman et al , 1995.*
(Continued)

*Primary Examiner* — Rita Desai
(74) *Attorney, Agent, or Firm* — Oblon, McClelland, Maier & Neustadt, L.L.P.

(57) ABSTRACT

The invention relates to novel compounds useful as ligands of actinides and which meet general formula (I) hereinafter:

(I)

where:

$R_1$ and $R_2$=H, a $C_1$ to $C_{12}$ hydrocarbon group, a monocyclic aryl or aryl-($C_1$ to $C_6$)alkyl group;

$R_3$, $R_4$, $R_5$ and $R_6$=H; a $C_1$ to $C_{12}$ hydrocarbon group; a monocyclic aryl or aryl-($C_1$ to $C_6$)alkyl group; a —$NR_7R_8$ or —$NR_7COR_8$ group where $R_7$=H, a $C_1$ to $C_{12}$ hydrocarbon group, a monocyclic aryl or aryl-($C_1$ to $C_6$)alkyl group, while $R_8$=a $C_1$ to $C_{12}$ hydrocarbon group, a monocyclic aryl or aryl-($C_1$ to $C_6$)alkyl group; an —$OR_9$ or —$SR_9$ group where $R_9$=a $C_1$ to $C_{12}$ hydrocarbon group, a monocyclic $C_6$ aryl or aryl-($C_1$ to $C_6$)alkyl group.

A further subject of the invention is a method for synthesizing these compounds and the uses thereof.

11 Claims, 1 Drawing Sheet

(51) Int. Cl.

| | |
|---|---|
| ***C22B 3/36*** | (2006.01) |
| ***G21C 19/42*** | (2006.01) |
| ***G21C 19/44*** | (2006.01) |
| ***G21C 19/46*** | (2006.01) |
| ***C22B 60/04*** | (2006.01) |

(52) U.S. Cl.

CPC ............... *G21C 19/42* (2013.01); *G21C 19/44* (2013.01); *G21C 19/46* (2013.01); *C22B 60/026* (2013.01); *C22B 60/04* (2013.01)

(56) References Cited

U.S. PATENT DOCUMENTS

2011/0002823 A1 1/2011 Miguirditchian et al.
2012/0186396 A1 7/2012 Marie et al.
2012/0247276 A1 10/2012 Miguirditchian et al.
2013/0202501 A1 8/2013 Saudray et al.

OTHER PUBLICATIONS

French Preliminary Report issued Jul. 13, 2011, in French Patent Application No. 1152835 with English translation of category of cited documents.

Emma Aneheim, et al., “A TBP/BTBP-based GANEX Separation Process. Part 1: Feasibility”, Taylor & Francis Group, LLC, 28, 2010, pp. 437-458.

Masaki Yamada, et al., “Synthesis of 2,9-Dichloro-1,10-phenanthroline from N,N'-Annelated Phenanthrolinediones”, Bull. Chem. Soc. Jpn., vol. 63, No. 9 , Sep. 1990, pp. 2710-2712.

International Search Report Issued May 8, 2012 in PCT/EP12/055557 Filed Mar. 28, 2012.

* cited by examiner

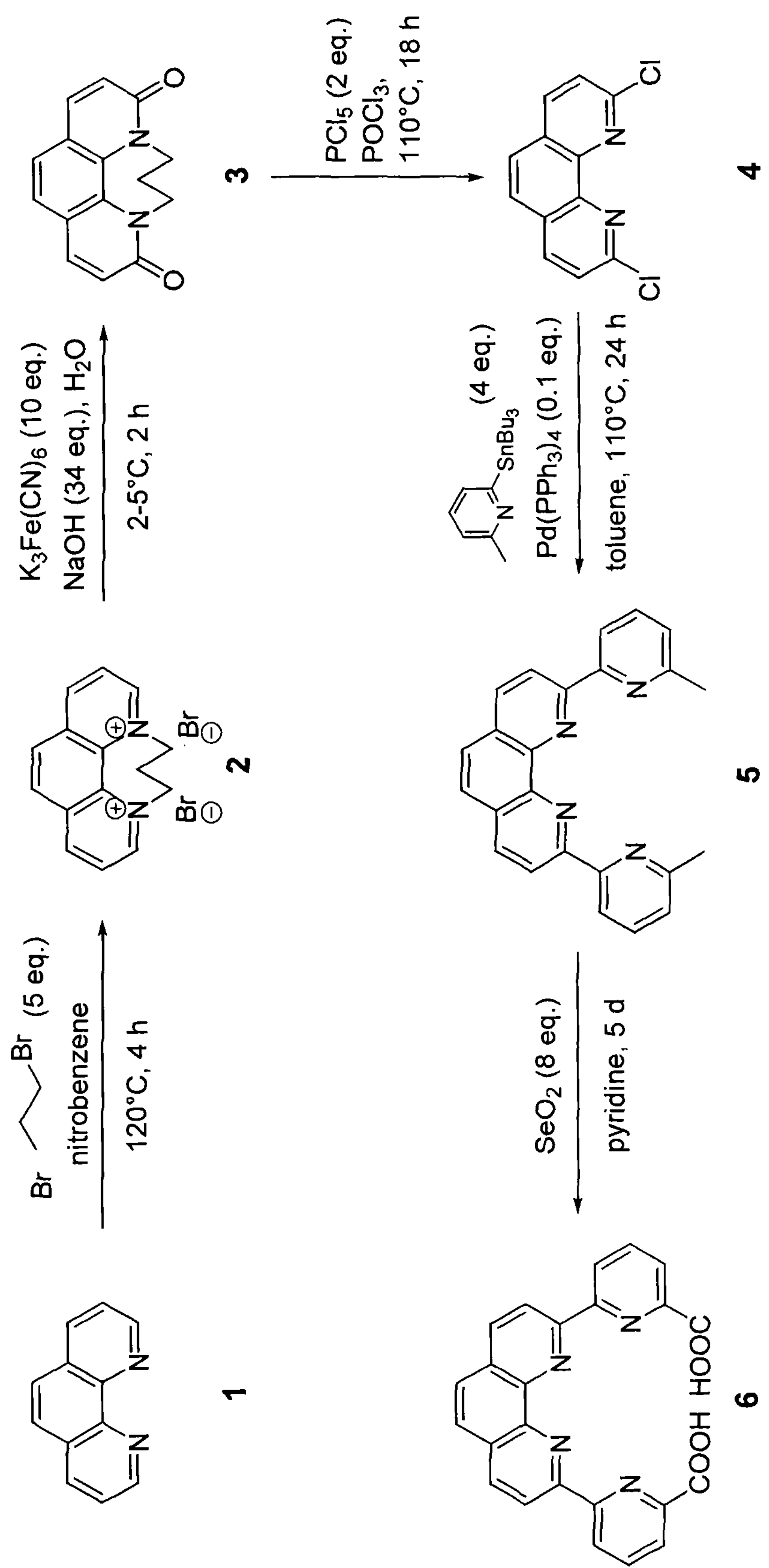
1
Br Br (5 eq.)
nitrobenzene
120°C, 4 h
2
$K_3Fe(CN)_6$ (10 eq.)
NaOH (34 eq.), $H_2O$
2-5°C, 2 h
3
$PCl_5$ (2 eq.)
$POCl_3$,
110°C, 18 h
4
$SnBu_3$ (4 eq.)
$Pd(PPh_3)_4$ (0.1 eq.)
toluene, 110°C, 24 h
5
$SeO_2$ (8 eq.)
pyridine, 5 d
COOH HOOC
6

2,9-DIPYRIDYL-1,10-PHENANTHROLINE DERIVATIVES USEFUL AS ACTINIDE LIGANDS, METHOD FOR SYNTHESIZING SAME, AND USES THEREOF

TECHNICAL FIELD

The present invention relates to novel compounds which are derivatives of 2,9-dipyridyl-1,10-phenanthroline and are useful as ligands of actinides.

It also pertains to a method allowing the synthesis of these compounds and to the uses thereof.

The compounds of the invention are capable alone, i.e. in the absence of any other extracting molecule, of extracting the actinides (III), (IV), (V) and (VI) from a highly acid aqueous solution in much more efficient manner than they extract the lanthanides.

In this respect they can therefore be used for the grouped separating of all the actinides (uranium, neptunium, plutonium, americium and/or curium) that are present in an acid aqueous solution such as a dissolution solution of a spent nuclear fuel, from the lanthanides also contained in this solution.

In addition, the derivatives of the invention have more pronounced affinity for americium than for curium.

They can therefore also be used to separate the americium present in a highly acid aqueous solution, such as a raffinate of the type produced during the first cycle of the PUREX process or COEX™ process, from the curium also contained in this solution.

STATE OF THE PRIOR ART

Numerous extracting molecules have been studied with the objective of separating the actinides contained in dissolution solutions of spent nuclear fuels from the lanthanides also contained therein.

One of the major difficulties is that of finding molecules which are capable of extracting the actinides in much more efficient manner than they extract the lanthanides, bearing in mind that firstly the lanthanides are present in dissolution solutions of spent nuclear fuels in much higher quantities than the actinides, and secondly that this type of solution typically has strong acidity, i.e. in general equal to or higher than 3 mol/L of nitric acid.

For grouped separating plutonium, neptunium, americium, curium (and possibly uranium) from the lanthanides present in a dissolution solution of a spent nuclear fuel, two methods have been proposed which use several steps, the first being an extraction using extractants such as a mixture of malonamide like N,N'-dimethyl-N,N'-dioctylhexylethoxymalonamide (or DMDOHEMA) with an alkylphosphoric acid like di-(2-ethylhexyl)phosphoric acid (or HDEHP), or a diglycolamide such as N,N,N',N'-tetraoctyl-3-oxapentanediamide (or TODGA).

These methods are respectively described in International PCT applications published under numbers WO 2007/118904 (reference [1]) and WO 2008/049807 (reference [2]).

Extractants which have donor oxygen atoms, such as the malonamides and the diglycolamides, do not however allow extracting the actinides from an acid aqueous solution containing both actinides and lanthanides, without at the same time extracting the lanthanides.

On this account, the methods described in the aforementioned references comprise firstly a step aimed at co-extracting the actinides and the lanthanides from the aqueous solution in which they are contained, by means of an organic phase containing the malonamide or the diglycolamide.

This co-extraction step is followed by a step aimed at selectively stripping the actinides from the organic phase, this being conducted by means of a weakly acid aqueous phase, i.e. having a pH of between 2 and 3 and containing a complexing agent, e.g. a polyamino-carboxylic acid. The lanthanides are then retained in the organic phase either due to the presence in this organic phase of an acid extractant of phosphoric acid type (reference [1]) or due to the presence in the weakly acid aqueous phase of nitrate ions (reference [2]).

This is followed by a step aimed at stripping the lanthanides from the organic phase, firstly to recover these lanthanides in an aqueous phase able subsequently to be subjected to vitrifying operations, and secondly to deplete the organic phase of radioelements with a view to reuse thereof.

In addition, compounds are known which have a greater affinity for the actinides, and in particular for the actinides (III), than for the lanthanides.

These are nitrogen-containing polyaromatic compounds such as 2,2':6',2"-terpyridine and some of its alkylated derivatives, 2,4,6-tri(2-pyridinyl)-1,3,5-triazine (or TPTZ), 2,6-bis (pyridin-2-yl)-4-amino-1,3,5-triazine (or ADPTZ) and 2,6-bis(1,2,4-triazinyl)pyridines, picolinamides, dipicolinamides and bipyridines with amide substitutions.

However, none of these compounds appear to be able to be used in an industrial process for the grouped separating of the actinides contained in dissolution solutions of spent nuclear fuels, from the lanthanides also contained in these solutions.

Indeed:

- either these compounds are quite simply incapable alone (i.e. in the absence of another extracting molecule) of extracting the actinides from an aqueous phase, and in particular from a highly acid aqueous phase, which is the case for example with 2,2':6',2"-terpyridine and its alkylated derivatives TPTZ, ADPTZ and the picolinamides which only extract the actinides under low acidity and in a synergic mixture with another extractant, typically α-bromodecanoic acid;
- or the load capacity of these compounds is too low, which is the case for example with 2,6-bis(1,2,4-triazinyl)pyridines;
- or they need to be in solution in a polar, halogenated and toxic diluent such as chloroform or meta-nitrotrifluorotoluene, which is the case for example with the dipicolinamides; yet this type of diluent cannot be used in an industrial process for treating spent nuclear fuels;
- or still they are proposed with the addition of an oxygenated donor extractant such as TBP (reference [3]), with the disadvantage of managing a multi-component organic solution and selecting a diluent such as cyclohexanone that is scarcely compatible with operations on an industrial scale.

Very recently, it was shown in the PCT international application published under number WO 2011/009814 (reference [4]), that terpyridines carrying amide groups can be used, in solution in n-octanol, to separate all the actinides(III), (IV), (V) and (VI) contained in a highly acid aqueous solution ($[HNO_3]$=3 mol/L) from the lanthanides also contained in this solution.

However the coefficients of distribution of the actinides (III), i.e. americium and curium, obtained with these terpyridines are relatively low (≤0.018), which means that, if these molecules were to be used to separate all the actinides from the lanthanides in an industrial process for treating spent nuclear fuel, it would be necessary to perform a fairly high number of extraction stages to guarantee total separation of the actinides(III) from the lanthanides.

The Inventors therefore set themselves the objective of finding novel compounds which are not only capable of extracting the whole of the actinides present in an acid aqueous solution, and in particular in an aqueous solution of high acidity, more efficiently than they extract the lanthanides, but which also allow obtaining for the actinides(III) coefficients of distribution significantly higher than those obtained for these same actinides in aforementioned reference [4].

The Inventors also set themselves the objective that these compounds should be able to be used in solution in a non-aqueous diluent compatible with an industrial process for treating spent nuclear fuels.

DESCRIPTION OF THE INVENTION

These objectives and others are achieved with the invention which firstly proposes a compound meeting the general formula (I) hereinafter:

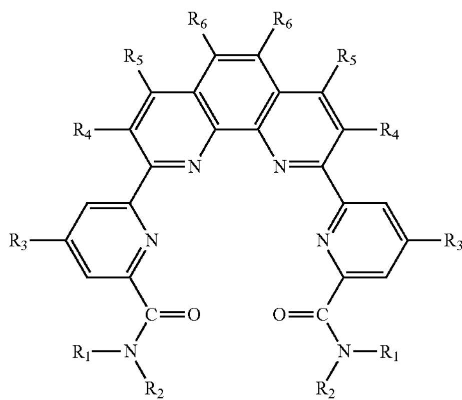

in which:

$R_1$ and $R_2$, either identical or different, represent a hydrogen atom, a $C_1$ to $C_{12}$ saturated or unsaturated, straight-chain or branched hydrocarbon group, or a monocyclic aryl or aryl-($C_1$ to $C_6$)alkyl group;

$R_3$, $R_4$, $R_5$ and $R_6$, either identical or different, represent:
- a hydrogen atom; or
- a $C_1$ to $C_{12}$ saturated or unsaturated, straight-chain or branched hydrocarbon group; or
- a monocyclic aryl or aryl-($C_1$ to $C_6$)alkyl group; or
- a —$NR_7R_8$ or —$NR_7COR_8$ group in which $R_7$ represents a hydrogen atom, a $C_1$ to $C_{12}$ saturated or unsaturated, straight-chain or branched hydrocarbon group, or a monocyclic aryl or aryl-($C_1$ to $C_6$)alkyl group, whilst $R_8$ represents a $C_1$ to $C_{12}$ saturated or unsaturated, straight-chain or branched hydrocarbon group or a monocyclic aryl or aryl-($C_1$ to $C_6$)alkyl group; or still
- an —$OR_9$ or —$SR_9$ group in which $R_9$ represents a $C_1$ to $C_{12}$ saturated or unsaturated, straight-chain or branched hydrocarbon group, or a monocyclic aryl or aryl-($C_1$ to $C_6$)alkyl group.

Therefore, the compound of the invention is a hexadented bi-functional ligand which comprises both a nitrogenous polyheterocyclic repeat unit, here a 2,9-dipyridyl-1,10-phenanthroline repeat unit, and two —$CONR_1R_2$ amide groups respectively carried by the pyridyl groups of said nitrogenous polyheterocyclic repeat unit.

In the foregoing and in the remainder hereof, by "$C_1$ to $C_{12}$ saturated or unsaturated, straight-chain or branched hydrocarbon group" is meant any alkyl group, straight-chain or branched, which comprises a least 1 carbon atom but no more than 12 carbon atoms, and any alkenyl or alkynyl group, straight-chain or branched, which comprises at least 2 carbon atoms and no more than 12 carbon atoms.

Such hydrocarbon groups are for example the following groups: methyl, ethyl, n-propyl, isopropyl, butyl such as n-butyle, sec-butyl, isobutyl or tert-butyl, pentyl such as n-pentyl, sec-pentyl or isopentyl, hexyl such as n-hexyl or isohexyl, octyl such as n-octyl or isooctyl, decyl such as n-decyl or isodecyl, dodecyl, ethylenyl, propylenyl, butenyl, pentenyl, hexenyl, methylpentenyl, buta-1,3-dienyl, octenyl, dekenyl, dodekenyl, ethynyl, propynyl, butynyl, pentynyl, hexynyl, octynyl, dekynyl, dodekynyl, etc.

Also by "monocyclic aryl group" is meant any group which only contains one ring and whose ring meets Hückel's rule of aromaticity and therefore has a number of delocalized electrons $\pi$ equal to 4n+2, whilst by "monocyclic aryl-($C_1$ to $C_6$)alkyl group" is meant any alkyl group, straight-chain or branched, which comprises at least one carbon atom but no more than 6 carbons atoms and one of the carbon atoms is substituted by an aryl group such as previously defined.

Such aryl groups are for example the phenyl group and the ortho-, meta- and para-tolyl groups whilst such arylalkyl groups are for example the following groups: benzyl, phenethyl, phenylpropyl, phenylbutyl, phenylpentyl, phenylhexyl, ortho-, meta- and para-tolylmethyl, ortho-, meta- and para-tolylethyl, ortho-, meta- and para-tolylpropyl, ortho-, meta- and para-tolylbutyl, ortho-, meta- and para-tolylpentyl, and ortho-, meta- and para-tolylhexyl.

According to the invention, the compound preferably meets the foregoing general formula (I) in which:

$R_1$ and $R_2$, either identical or different, represent a hydrogen atom, a $C_1$ to $C_{12}$ straight-chain or branched alkyl group or a monocyclic aryl group;

$R_3$, $R_4$, $R_5$ and $R_6$, either identical or different, represent:
- a hydrogen atom; or
- a $C_1$ to $C_{12}$ straight-chain or branched alkyl group; or
- a monocyclic aryl group; or
- a —$NR_7R_8$ or —$NR_7COR_8$ group in which $R_7$ represents a hydrogen atom, a $C_1$ to $C_{12}$ straight-chain or branched alkyl group, or a monocyclic aryl group, whilst $R_8$ represents a $C_1$ to $C_{12}$ straight-chain or branched alkyl group or a monocyclic aryl group; or still
- a —$OR_9$ or —$SR_9$ group in which $R_9$ represents a $C_1$ to $C_{12}$, straight-chain or branched alkyl group or a monocyclic aryl group.

Among these compounds, particular preference is given to those which meet the foregoing general formula (I) in which $R_3$, $R_4$, $R_5$ and $R_6$ represent a hydrogen atom for the simple reason that the synthesis of compounds whose 2,9-dipyridyl-1,10-phenanthroline repeat unit does not contain any substituent other than the two —$CONR_1R_2$ amide groups is generally easier to implement than for compounds whose 2,9-dipyridyl-1,10-phénanthroline repeat unit has more substitutions.

Also, more particular preference is given to compounds which meet the foregoing general formula (I) in which $R_1$ and $R_2$, either identical or different, represent either a $C_1$ to $C_{12}$, and better still $C_2$ to $C_{12}$, alkyl chain, or a phenyl group, or an ortho-, meta-ou para-tolyl group.

Such compounds are notably:
- N,N,N',N'-tetraethyl-6,6'-([1,10]-phenanthrolin-2,9-diyl)-pyridin-2-yldiamide, which meets the foregoing general formula (I) in which $R_1$ and $R_2$ represent an ethyl group whilst $R_3$, $R_4$, $R_5$ and $R_6$ represent a hydrogen atom;
- N,N,N',N'-tetrahexyl-6,6'-([1,10]-phenanthrolin-2,9-diyl)-pyridin-2-yldiamide, which meets the foregoing general formula (I) in which $R_1$ and $R_2$ represent an n-hexyl group whilst $R_3$, $R_4$, $R_5$ and $R_6$ represent a hydrogen atom;

N,N,N',N'-tetraoctyl-6,6'-([1,10]-phenanthrolin-2,9-diyl)-pyridin-2-yldiamide, which meets the foregoing general formula (I) in which $R_1$ and $R_2$ represent an n-octyl group whilst $R_3$, $R_4$, $R_5$ and $R_6$ represent a hydrogen atom;

N,N,N',N'-tetradecyl-6,6'-([1,10]-phenanthrolin-2,9-diyl)-pyridin-2-yldiamide, which meets the foregoing general formula (I) in which $R_1$ and $R_2$ represent an n-decyl group whilst $R_3$, $R_4$, $R_5$ and $R_6$ represent a hydrogen atom;

N,N,N',N'-tetradodecyl-6,6'-([1,10]-phenanthrolin-2,9-diyl)-pyridin-2-yldiamide, which meets the foregoing general formula (I) in which $R_1$ and $R_2$ represent an n-octyl group whilst $R_3$, $R_4$, $R_5$ and $R_6$ represent a hydrogen atom;

N,N'-diethyl-N,N'-diphenyl-6,6'-([1,10]-phenanthrolin-2,9-diyl)-pyridin-2-yldiamide, which meets the foregoing general formula (I) in which $R_1$ represents an ethyl group, $R_2$ represents a phenyl group whilst $R_3$, $R_4$, $R_5$ and $R_6$ represent a hydrogen atom;

N,N'-dihexyl-N,N'-diphenyl-6,6'-([1,10]-phenanthrolin-2,9-diyl)-pyridin-2-yldiamide, which meets the a foregoing general formula (I) in which $R_1$ represents an n-hexyl group, $R_2$ represents a phenyl group whilst $R_3$, $R_4$, $R_5$ and $R_6$ represent a hydrogen atom;

N,N'-dioctyl-N,N'-diphenyl-6,6'-([1,10]-phenanthrolin-2,9-diyl)-pyridin-2-yldiamide, which meets the foregoing general formula (I) in which $R_1$ represents an n-octyl group, $R_2$ represents a phenyl group whilst $R_3$, $R_4$, $R_5$ and $R_6$ represent a hydrogen atom;

N,N'-didecyl-N,N'-diphenyl-6,6'-([1,10]-phenanthrolin-2,9-diyl)-pyridin-2-yldiamide, which meets the foregoing general formula (I) in which $R_1$ represents a n-decyl group, $R_2$ represents a phenyl group whilst $R_3$, $R_4$, $R_5$ and $R_6$ represent a hydrogen atom; and N,N'-didodecyl-N,N'-diphenyl-6,6'-([1,10]-phenanthrolin-2,9-diyl)-pyridin-2-yldiamide, which meets the foregoing general formula (I) in which $R_1$ represents an n-dodecyl group, $R_2$ represents a phenyl group whilst $R_3$, $R_4$, $R_5$ and $R_6$ represent a hydrogen atom.

The compounds of the invention may in particular be obtained using a method which comprises the following steps:

reacting a compound meeting the general formula (II) hereinafter:

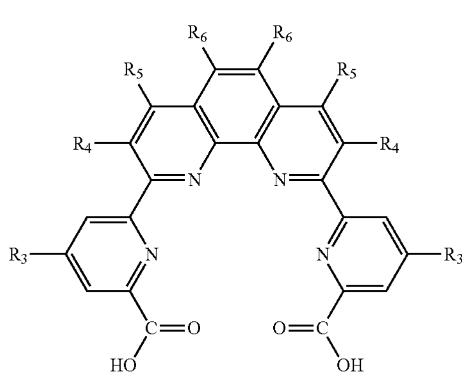

in which $R_3$, $R_4$, $R_5$ and $R_6$, either identical or different, have the same meaning as in the foregoing general formula (I), with a halogenation reagent to obtain a compound meeting the general formula (III) hereinafter:

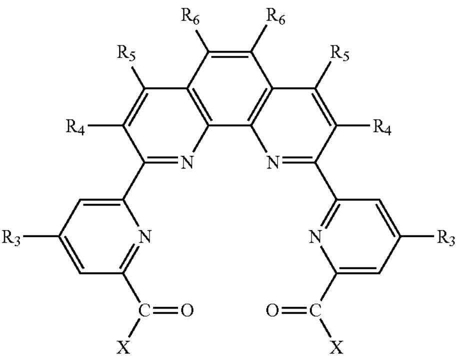

in which $R_3$, $R_4$, $R_5$ and $R_6$, either identical or different, have the same meaning as in the foregoing general formula (II), whilst X represents a chlorine atom; followed by reacting the compound meeting the foregoing general formula (III) with an amine of formula $HNR_1R_2$ in which $R_1$ and $R_2$ have the same meaning as in the foregoing general formula (I), this reaction taking place in the presence of a base and in an aprotic polar solvent.

Therefore, a further subject of the invention is a synthesis method such as described above.

In this method, the halogenation reagent may in particular be thionyl chloride, phosphorus oxichloride or phosphorus trichloride; the base may in particular be triethylamine, diisopropylethylamine or pyridine, whilst the aprotic polar solvent may in particular be dichloromethane, acetonitrile or dimethylsulfoxide.

It is evidently also possible to obtain the compounds of the invention from a compound meeting the foregoing general formula (II) by subjecting the latter to reactions other than those just described.

For example, the compounds of the invention can also be obtained by reacting a compound meeting the foregoing general formula (II) with an amine of formula $HNR_1R_2$ in which $R_1$ and $R_2$ have the same meaning as in the foregoing general formula (I), in the presence of a peptide coupling agent such as 1-ethyl-3-[3-dimethylaminopropyl]-carbodiimide hydrochloride and a peptide coupling catalyst such as N-hydroxybenzotriazole, in solution in an organic aprotic polar solvent of the aforementioned types.

Whatever the case, the compound meeting the foregoing general formula (II) can be obtained by:

coupling, using Stille's method, a compound of 1,10-phenanthroline substituted at positions 2.9 by a halogen atom, e.g. chlorine, with a compound of 2-methylpyridine substituted by an organostannic group, e.g. a tri-n-butyl tin group, in the presence of a palladium catalyst; or any other organocatalysed coupling method to form Carbon-Carbon bonds between two heterocyclic reagents of Negishi, Suzuki or Ullmann coupling type; then oxidizing the compound thus obtained using an oxidizing agent of selenium dioxide type, in an aprotic polar solvent such as pyridine.

With regard to the compound of 1,10-phenanthroline substituted at positions 2.9 by a halogen atom, this can be obtained from 1,10-phenanthroline using the protocol described by Yamada et al., in reference [5].

The compounds of the invention have particularly high affinity for actinides at their different degrees of oxidation.

More particularly, the compounds of the invention are capable of extracting all the actinides(III), (IV), (V) and (VI) from an acid aqueous phase, and in particular from a highly acid aqueous phase such as a nitric acid solution of molarity equal to or higher than 2.

These actinides may notably be americium(III) and curium (III), plutonium(IV), neptunium(V), neptunium(VI) and uranium(VI).

Therefore, a further subject of the invention is the use of a compound such as previously defined as a ligand of one or more actinides, and in particular the use of this compound to extract one or more actinides from an acid aqueous solution.

As part of these uses, the compound of the invention may particularly be used to separate all the actinides contained in an acid aqueous solution from the lanthanides also contained in this solution.

Such an acid aqueous solution may particularly be a solution resulting from the dissolution of a spent nuclear fuel in nitric acid.

However, it may also be a solution resulting from the dissolution of a spent nuclear fuel in nitric acid which has previously been rid of the uranium it initially contained.

The compound of the invention may also be used to separate the americium present in an acid aqueous solution from the curium which is also contained in this solution.

Said acid aqueous solution may notably be a raffinate of those types produced during the first cycle of the PUREX process or COEX™ process which contain americium, curium and lanthanides but which no longer contain either uranium or plutonium or neptunium.

The use of the compound of the invention to separate all the actinides present in an acid aqueous solution from the lanthanides also contained in this solution typically comprises the following steps:

- extracting all the actinides from the acid aqueous solution by contacting this solution with an organic phase comprising this compound, then separating said aqueous solution and said organic phase; and
- stripping all the actinides contained in the organic phase obtained at the end of the extraction step, by contacting this organic phase with an acid aqueous phase, preferably scarcely acidic, i.e. typically of pH ranging from 2 to 3, and optionally comprising one or more complexing agents, then separating said organic and aqueous phases.

Regarding the use of the compound of the invention to separate the americium present in an acid aqueous solution from the curium also contained in this solution, this typically comprises the following steps:

- extracting the americium from the acid aqueous solution by contacting this aqueous solution with an organic phase comprising the compound, then separating said aqueous solution and said organic phase; and
- stripping the americium contained in the organic phase obtained at the end of the extraction step, by contacting this organic phase with an acid aqueous phase preferably of low acidity, i.e. typically of pH ranging from a 2 to 3, and optionally comprising one or more complexing agents, then separating said organic and aqueous phases.

Whatever the case, the compound is advantageously used in solution to the proportion of 0.001 to 0.5 mol/L, in an organic diluent which is preferably chosen from among n-octanol, n-dodecane and hydrogenated tetrapropylene.

Other characteristics and advantages of the invention will become better apparent on reading the remainder of the description below which refers to examples describing the synthesis of compounds conforming to the invention and demonstrating their extracting properties.

Of course, these examples are only given to illustrate the subject of the invention and are in no way limiting with respect to this subject.

BRIEF DESCRIPTION OF THE FIGURE

FIG. 1 illustrates the reaction scheme used for the synthesis of the compounds of the invention.

DETAILED DESCRIPTION OF PARTICULAR EMBODIMENTS

Example 1

Synthesis of Compounds of the Invention

The synthesis was performed of the compounds of the invention, namely:

- N,N,N',N'-tetraoctyl-6,6'-([1,10]-phenanthrolin-2,9-diyl)-pyridin-2-yldiamide, denoted todi(ampyr)phen hereinafter, which meets the foregoing general formula (I) in which $R_1=R_2=C_8H_{17}$ and $R_3=R_4=R_5=R_6=H$; and
- N,N'-dihexyl-N,N'-diphenyl-6,6'-([1,10]-phenanthrolin-2,9-diyl)-pyridin-2-yldiamide, denoted dihexphdi (ampyr)phen hereinafter, which meets the foregoing general formula (I) in which $R_1=C_6H_{13}$, $R_2$=phenyl and $R_3=R_4=R_5=R_6=H$;
- N,N,N',N'-tetraethyl-6,6'-([1,10]-phenanthrolin-2,9-diyl)-pyridin-2-yldiamide, denoted dietdi(ampyr)phen hereinafter, which meets the foregoing general formula (I) in which $R_1=R_2=C_2H_5$ and $R_3=R_4=R_5=R_6=H$;
- N,N'-diethyl-N,N'-diphenyl-6,6'-([1,10]-phenanthrolin-2,9-diyl)-pyridin-2-yldiamide, denoted dietphdi(ampyr) phen hereinafter, which meets the foregoing general formula (I) in which $R_1=C_2H_5$, $R_2$=phenyl and $R_3=R_4=R_5=R_6=H$; from 6,6'-(2,9-dipyridyl-1,10-phenanthroline) acid, denoted compound 6 hereinafter.

1.1. Synthesis of Compound 6

Compound 6 is previously obtained from 1,10-phenanthroline, denoted compound 1 hereinafter, following the reaction scheme illustrated in FIG. 1.

Compound 1 is commercially available.

Compounds 2, 3 and 4 are obtained following the protocol described by Yamada et al. in aforementioned reference [5].

Therefore, compound 2 is obtained by treating compound 1 with a large excess of 1,3-dibromopropane (5 eq.) in nitrobenzene under reflux, at 120° C. and for 4 hours, and then recrystallizing the product obtained in a 75:25 mixture of ethanol/water. The yield is 98%.

Compound 3 is obtained by oxidizing compound 2 with potassium ferricyanide (10 eq.) in an aqueous sodium hydroxide solution (34 eq.), at a temperature of between 2 and 5° C. The yield is 41%.

Next, compound 4 is obtained by treating compound 3 with phosphorus pentachloride (2 eq.) in phosphorus oxichloride, at 110° C. for 18 hours. The yield is 88%.

Compound 4 thus obtained reacts under Stille's coupling conditions with 2-methyl-6-(tributylstannyl)pyridin (4 eq.). This reaction is catalysed by a palladium complex (tetrakis-(triphenylphosphine palladium—$Pd(PPh_3)_4$—0.1 eq.) which, after a reaction time of 24 hours under reflux in toluene at 110° C., leads to compound 5 with a yield of 85%.

Finally, oxidation of compound 5 with excess selenium dioxide (8 eq.) in pyridine under reflux for 5 days allows compound 6 to be obtained with a yield of 98%.

1.2. Synthesis of Todi(ampyr)phen

Todi(ampyr)phen is obtained by reaction of compound 6 with di-n-octylamine.

To do so, a solution of 395 mg (0.9 mmol, 1.0 eq.) of compound 6 in 8 mL of thionyl chloride ($SOCl_2$) is heated to 90° C. for 2 hours. After evaporation of the thionyl chloride, the residue is dissolved in 10 mL of dichloromethane ($CH_2Cl_2$) and cooled to 0° C. The dropwise addition is then made of 569 mg (5.6 mmol, 6.0 eq.) triethylamine ($Et_3N$) and 677 mg (2.8 mmol, 3.0 eq.) of di-n-octylamine and the mixture is agitated for 4 hours at ambient temperature in an argon atmosphere. After evaporation to dryness, the crude product is dissolved in dichloromethane and washed 3 times by contact with distilled water. The organic phase is dried over sodium sulfate ($Na_2SO_4$) and the solvent is evaporated. The residue obtained is purified by silica gel chromatography (elution with a 40:60 petroleum ether/ethyl acetate mixture).

After evaporation of the solvents, 475 mg of todi(ampyr)phen are obtained in the form of a yellow oil. The yield is 58%.

Empirical formula: $C_{56}H_{80}N_6O_2$

Molar mass: 868 g/mol $^1$H NMR (400 MHz, $CDCl_3$) δ ppm: 9.12 (d, $^3$J=7.8, 2H, $H_6$), 8.84 (d, $^3$J=8.4, 2H, $H_3$), 8.38 (d, $^3$J=8.4, 2H, $H_2$), 8.08 (t, $^3$J=7.8, 1H, $H_5$), 7.87 (s, 2H, $H_1$), 7.69 (d, $^3$J=7.8, 2H, $H_4$), 3.56 (q, $^3$J=7.8, 4H, $2CH_2$), 3.38 (q, $^3$J=7.8, 4H, $2CH_2$), 1.73 (m, 8H, $4CH_2$), 1.37 (m, 20H, $10CH_2$), 1.27 (m, 20H, $10CH_2$), 1.09 (t, $^3$J=6.9, 6H, $2CH_3$), 0.74 (t, $^3$J=6.9, 6H, $2CH_3$)

$^{13}$C NMR (400 MHz, $CDCl_3$) δ ppm: 168.8 (2CO), 155.6 (2Cq), 154.7 (2Cq), 154.6 (2Cq), 145.6 (2Cq), 137.9 ($2CH_5$), 137.0 ($2CH_2$), 129.2 (2Cq), 126.8 ($2CH_1$), 123.7 ($2CH_4$), 122.4 ($2CH_6$), 120.8 ($2CH_3$), 49.1 ($2CH_2$), 46.0 ($2CH_2$), 31.8 ($2CH_2$), 31.6 ($2CH_2$), 29.4 ($2CH_2$), 29.3 ($2CH_2$), 29.2 ($4CH_2$), 29.1 ($2CH_2$), 27.6 ($2CH_2$), 27.1 ($2CH_2$), 26.7 ($2CH_2$), 22.6 ($2CH_2$), 22.5 ($2CH_2$), 14.1 ($2CH_3$), 13.9 ($2CH_3$)

Mass Spectrometry (EI), m/z (1%): 868.7 ($M^+$, 34%), 601.4 ($M^+$-$CONOct_2$, 17%), 334.1 ($M^+$-$2CONOct_2$, 100%)

1.3. Synthesis of Dihexphdi(ampyr)phen

Dihexphdi(ampyr)phen is obtained following the same protocol as described under item 1.2 above but by reacting compound 6 with N-hexylaniline (3 eq.) instead of di-n-octylamine.

The compound dihexphdi(ampyr)phen is obtained in the form of a beige powder with a yield of 58%.

Empirical formula: $C_{48}H_{48}N_6O_2$

Molar mass: 740 g/mol

Melting point: 168° C.

$^1$H NMR (400 MHz, $CDCl_3$) δ ppm: 8.85 (d, $^3$J=7.2, 2H, $H_6$), 8.20 (m, 4H, $H_2$, $H_3$), 7.91 (m, 2H, $H_5$), 7.79 (s, 2H, $H_4$), 7.75 (d, $^3$J=7.2, 2H, $H_4$), 7.15 (m, 8H, $H_7$, $H_8$), 7.01 (m, 2H, $H_9$), 4.01 (m, 4H, $2CH_2$), 1.70 (m, 4H, $2CH_2$), 1.31 (m, 12H, $6CH_2$), 0.88 (m, 6H, $2CH_3$)

$^{13}$C NMR (400 MHz, $CDCl_3$) δ ppm: 168.0 (2CO), 155.1 (2Cq), 154.0 (2Cq), 153.2 (2Cq), 145.1 (2Cq), 143.6 (2Cq), 137.4 ($2CH_5$), 136.7 ($2CH_2$ or $2CH_3$), 129.0 (2Cq), 128.7 ($2CH_7$ or $2CH_8$), 127.6 ($2CH_7$ or $2CH_8$), 126.6 ($2CH_1$), 126.4 ($2CH_9$), 124.6 ($2CH_4$), 122.2 ($2CH_6$), 120.8 ($2CH_2$ or $2CH_3$), 50.5 ($2CH_2$), 31.5 ($2CH_2$), 27.5 ($2CH_2$), 26.6 ($2CH_2$), 22.5 ($2CH_2$), 14.0 ($2CH_3$)

Mass spectrometry (EI), m/z (1%): 740.2 ($M^+$, 14%), 334.1 ($M^+$-2CONHexPh, 100%)

1.4. Synthesis of Dietdi(ampyr)phen

Dietdi(ampyr)phen is obtained following the same protocol as described under item 1.2 above but by reacting compound 6 with diethylamine (3 eq.) instead of di-n-octylamine.

The compound dietdi(ampyr)phen is obtained in the form of a white powder with a yield of 52%.

Empirical formula: $C_{32}H_{32}N_{16}O_2$

Molar mass: 532 g/mol

Melting point: 201° C.

$^1$H NMR (400 MHz, $CDCl_3$) δ ppm: δ 9.11 (dd, $^3$J=7.8, $^4$J=0.6, 2H, $H_6$), 8.88 (d, $^3$J=8.4, 2H, $H_3$), 8.42 (d, $^3$J=8.4, 2H, $H_2$), 8.10 (t, $^3$J=7.8, 2H, $H_5$), 7.89 (s, 2H, $H_1$), 7.72 (dd, $^3$J=7.8, $^4$J=0.6, 2H, $H_4$), 3.65 (q, $^3$J=6.9, 4H, $2CH_2$), 3.47 (q, $^3$J=6.9, 4H, $2CH_2$), 1.34 (t, $^3$J=6.9, 6H, $2CH_3$), 1.27 (t, $^3$J=6.9, 6H, $2CH_3$)

$^{13}$C NMR (400 MHz, $CDCl_3$) δ ppm: δ 168.2 (2CO), 155.1 (2Cq), 154.2 (2Cq), 154.1 (2Cq), 145.0 (2Cq), 137.6 ($2C_5$), 136.9 ($2C_2$), 128.8 (2Cq), 126.5 ($2C_1$), 123.3 ($2C_4$), 122.2 ($2C_6$), 120.5 ($2C_3$), 42.9 ($2CH_2$), 39.9 ($2CH_2$), 14.1 ($2CH_3$), 12.5 ($2CH_3$)

Mass spectrometry (EI), m/z (1%): 532 ($M^+$, 42%), 334 ($M^+$-$CONEt_2$, 100%)

1.5. Synthesis of Dietphdi(ampyr)phen

Dietphdi(ampyr)phen is obtained following the same protocol as described under item 1.2 above but by reacting compound 6 with N-ethylaniline (3 eq.) instead of di-n-octylamine.

The compound dietphdi(ampyr)phen is obtained in the form of a white powder with a yield of 31%.

Empirical formula: $C_{40}H_{32}N_6O_2$

Molar mass: 628 g/mol

Melting point: >230° C.

$^1$H NMR (400 MHz, $CDCl_3$) δ ppm: δ 8.90 (d, $^3$J=7.8, 2H, $H_6$), 8.35 (m, 4H, $H_2$, $H_3$), 7.95 (t, $^3$J=7.8, 2H, $H_5$), 7.86 (s, 2H, $H_1$), 7.77 (d, $^3$J=7.8, 2H, $H_4$), 7.16 (m, 8H, $H_2$, $H_8$), 7.03 (m, 2H, $H_9$), 4.11 (q, $^3$J=7.2, 4H, $CH_2$), 1.31 (t, $^3$J=7.2, 6H, $CH_3$)

$^{13}$C NMR (400 MHz, $CDCl_3$) δ ppm: δ 167.8 (2CO), 155.2 (2Cq), 154.2 (2Cq), 153.1 (2Cq), 145.2 (2Cq), 143.4 (2Cq), 137.4 ($2C_5$), 136.6 ($2C_2$ or $2 C_3$), 129.0 (2Cq), 128.8 ($4C_7$ or $4C_8$), 127.7 ($4C_7$ or $4C_8$), 126.6 ($2C_1$), 126.5 ($2C_9$), 124.6 ($2C_4$), 122.3 ($2C_6$), 120.8 ($2C_2$ or $2C_3$), 45.5 ($2CH_2$), 12.8 ($2CH_3$)

Mass spectrometry (EI), m/z (1%): 628 ($M^+$, 21%), 418 ($M^+$-CONEtPh, 14%), 334 ($M^+$-2CONEtPh, 100%)

Example 2

Extractant Properties of the Compounds of the Invention

Liquid-liquid extractions were performed using:

- as organic phases: two solutions one comprising todi(ampyr)phen and the other comprising dihexphdi(ampyr)phen at 0.01 mol/L in n-octanol; and
- as aqueous phases: three aqueous hereinafter denoted S1, S2 and S3 and respectively comprising:

S1: a mixture of $^{239-240}$Pu(IV), $^{241}$Am(III), $^{244}$Cm(III) and $^{152}$Eu(III), all in trace state, i.e. at $10^{-5}$ to $10^{-6}$ mol/L, in 3 mol/L nitric acid;

S2: $^{237}$Np(V) at $5\cdot10^{-4}$ mol/L in 3 mol/L nitric acid;

S3: $^{238}$U(VI) at $5\cdot10^{-3}$ mol/L in 3 mol/L nitric acid.

Each organic phase was placed in contact with each of the aqueous phases S1, S2 and S3, in the proportion of one volume of organic phase per one volume of aqueous phase, and the phases thus contacted were left under mechanical agitation for one hour at a constant temperature of 25° C.

Thereafter the organic and aqueous phases were separated from each other and the activities of the different radioelements were determined in each of these phases by a spectrometry, γ spectrometry or X fluorescence accordingly.

Table I below gives, for each type of organic phase and for each extraction, the coefficients of distribution of plutonium (IV), americium(III), curium(III), europium(III), neptunium (V) and uranium(VI) obtained from the activities thus determined, whilst Table II below gives, for each type of organic phase, the separation factors $FS_{Pu/Eu}$, $FS_{Am/Eu}$, $FS_{Cm/Ce}$ and $FS_{Am/Cm}$ obtained from these coefficients de distribution.

It is recalled that in the field of liquid-liquid extractions, the coefficient of distribution, denoted $D_M$, of an element M corresponds to the ratio, at equilibrium, of the concentrations (here represented by the activities) of this element in the contacted organic and aqueous phases, and that the separation factor between two metal elements M1 and M2, denoted $FS_{M1/M2}$, corresponds to $D_{M1}/D_{M2}$, i.e. to the ratio of the coefficients of distribution of the metal elements M1 and M2 obtained during one same extraction.

TABLE I

| | Organic phase | |
|---|---|---|
| $D_M$ | todi(ampyr)phen | dihexphdi(ampyr)phen |
| $D_{Pu(IV)}$ | 2.17 | 14.80 |
| $D_{Am(III)}$ | 0.17 | 1.75 |
| $D_{Cm(III)}$ | 0.07 | 0.74 |
| $D_{Eu(III)}$ | 0.0063 | 0.091 |
| $D_{Np(V)}$ | 11.01 | 16.60 |
| $D_{U(VI)}$ | 1.92 | >2 |

TABLE II

| | Organic phase | |
|---|---|---|
| $FS_{M1/M2}$ | todi(ampyr)phen | dihexphdi(ampyr)phen |
| $FS_{Pu/Eu}$ | 349 | 166 |
| $FS_{Am/Eu}$ | 25 | 19 |
| $FS_{Cm/Eu}$ | 10 | 8 |
| $FS_{Am/Cm}$ | 2.3 | 2.3 |

These tables show that the compounds of the invention extract the actinides(III), (IV), (V) and (VI) from an aqueous solution having high acidity (3 mol/L) much more efficiently than the terpyridines proposed in aforementioned reference [4] since:

- the coefficients of distribution of plutonium(IV) are all equal to or higher than 2;
- the coefficients of distribution of neptunium(V) are all equal to or higher than 11;
- the coefficients of distribution of uranium(VI) are all higher than 1.9; whilst
- the coefficients of distribution of americium and curium are all equal to or higher than 0.07.

These tables also show that the compounds of the invention extract the actinides(III) and (IV) from a said solution in much more efficient manner than they extract the lanthanides since:

- the separation factors between plutonium(IV) and europium are all higher than 160; whilst
- the separation factors between the actinides(III) and europium are all equal to or higher than 8.

These tables further show that the compounds of the invention have more pronounced affinity for americium than for curium since the coefficients of distribution of americium are all 2.3 times higher than those obtained for curium.

CITED REFERENCES

[1] International application PCT WO 2007/118904

[2] International application PCT WO 2008/049807

[3] Aneheim et al., *Solv. Ext. Ion Exch.* (2010), 28, 437-458

[4] International application PCT WO 2011/009814

[5] Yamada et al., *Bulletin of Chemical Society of Japan* (1990), 63, 2710-2712

The invention claimed is:

1. A compound of formula (I):

(I)

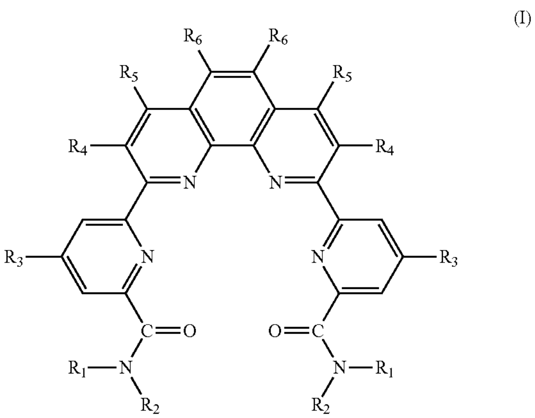

wherein:

$R_1$ and $R_2$ each independently represent a hydrogen atom, a $C_1$ to $C_{12}$ saturated or unsaturated, linear or branched hydrocarbon group, or a monocyclic aryl or aryl-($C_1$ to $C_6$)alkyl group; and $R_3$, $R_4$, $R_5$ and $R_6$ each independently represent a hydrogen atom.

2. The compound of claim 1, wherein:

$R_1$ and $R_2$ each independently represent a hydrogen atom, a $C_1$ to $C_{12}$ linear or branched alkyl group or a monocyclic aryl group.

3. The compound of claim 1, wherein $R_1$ and $R_2$ each independently represent a $C_1$ to $C_{12}$ alkyl chain, a phenyl group, or an ortho-, meta- or para-tolyl group.

4. The compound of claim 1, wherein the compound is selected from the group consisting of:

N,N,N',N'-tetraethyl-6,6'-([1,10]-phenanthrolin-2,9-diyl)-pyridin-2-yldiamide,

N,N,N',N'-tetrahexyl-6,6'-([1,10]-phenanthrolin-2,9-diyl)-pyridin-2-yldiamide,

N,N,N',N'-tetraoctyl-6,6'-([1,10]-phenanthrolin-2,9-diyl)-pyridin-2-yldiamide,

N,N,N',N'-tetradecyl-6,6'-([1,10]-phenanthrolin-2,9-diyl)-pyridin-2-yldiamide,

N,N,N',N'-tetradodecyl-6,6'-([1,10]-phenanthrolin-2,9-diyl)-pyridin-2-yldiamide, N,N'-diethyl-N,N'-diphenyl-6,6'-([1,10]-phenanthrolin-2,9-diyl)-pyridin-2-yldiamide, N,N'-dihexyl-N,N'-diphenyl-6,6'-([1,10]-phenanthrolin-2,9-diyl)-pyridin-2-yldiamide, N,N'-dioctyl-N,N'-diphenyl-6,6'-([1,10]-phenanthrolin-2,9-diyl)-pyridin-2-yldiamide, N,N'-didecyl-N,N'-diphenyl-6,6'-([1,10]-phenanthrolin-2,9-diyl)-pyridin-2-yldiamide, and N,N'-didodecyl-N,N'-diphenyl-6,6'-([1,10]-phenanthrolin-2,9-diyl)-pyridin-2-yldiamide.

5. A method for preparing the compound of claim 1, the method comprising:

reacting a compound of formula (II):

(II)

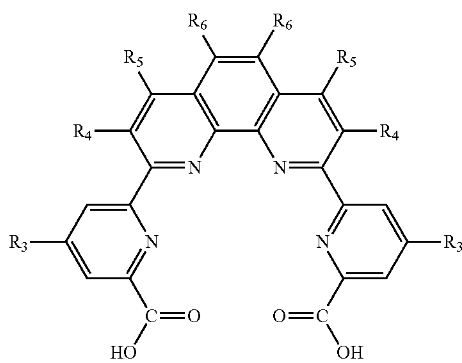

with a halogenation reagent, thereby obtaining a compound of formula (III):

(III)

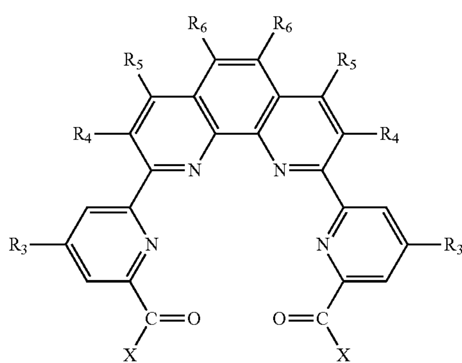

wherein X represents a halogen atom; and reacting the compound of formula (III) with an amine of formula $HNR_1R_2$ in an aprotic polar solvent in the presence of a base, thereby obtaining the compound of formula (I).

6. The method of claim 5, wherein the halogenation reagent is thionyl chloride, phosphorus oxichloride, or phosphorus trichloride, and the base is triethylamine, diisopropylethylamine, or pyridine.

7. A method for separating actinides from lanthanides in an acid aqueous solution, the method comprising:

extracting the actinides from the acid aqueous solution by contacting the acid aqueous solution with an organic phase comprising the compound of claim 1;

subsequently separating the acid aqueous solution from the organic phase, thereby obtaining an organic phase comprising the actinides;

subsequently stripping the actinides from the organic phase by contacting the organic phase with an acid aqueous phase; and subsequently separating the organic phase from the acid aqueous phase.

8. The method of claim 7, wherein the acid aqueous solution is obtained by dissolving a spent nuclear fuel in nitric acid.

9. The method of claim 7, wherein the acid aqueous solution is free of uranium.

10. The method of claim 7, wherein the compound is in a solution comprising an organic solvent selected from the group consisting of n-octanol, n-dodecane and hydrogenated tetrapropylene.

11. A method for separating americium from curium in an acid aqueous solution, the method comprising:

extracting the americium from the acid aqueous solution by contacting the acid aqueous solution with an organic phase comprising the compound of claim 1, subsequently separating the acid aqueous solution from the organic phase, thereby obtaining an organic phase comprising the americium;

stripping the americium from the organic phase by contacting the organic phase with an acid aqueous phase; and subsequently separating the organic phase from the acid aqueous phase.

* * * * *